(12) United States Patent
Stahl et al.

(10) Patent No.: US 11,260,227 B2
(45) Date of Patent: Mar. 1, 2022

(54) CROSS-CORRELATION THRESHOLD ESTIMATION METHOD (XTEM)

(71) Applicant: Oticon Medical A/S, Smørum (DK)

(72) Inventors: Pierre Stahl, Vallauris (FR); Dan Gnansia, Vallauris (FR)

(73) Assignee: OTICON MEDICAL A/S, Smørum (DK)

( * ) Notice: Subject to any disclaimer, the term of this patent is extended or adjusted under 35 U.S.C. 154(b) by 170 days.

(21) Appl. No.: 16/654,381

(22) Filed: Oct. 16, 2019

(65) Prior Publication Data

US 2020/0121928 A1    Apr. 23, 2020

(30) Foreign Application Priority Data

Oct. 17, 2018  (EP) .................................... 18200880

(51) Int. Cl.
  *A61N 1/36* (2006.01)
  *A61N 1/02* (2006.01)
  *A61B 5/38* (2021.01)
(52) U.S. Cl.
  CPC ......... *A61N 1/36039* (2017.08); *A61N 1/025* (2013.01); *A61B 5/38* (2021.01)
(58) Field of Classification Search
  CPC .................... A61N 1/36038; A61N 1/36039
  See application file for complete search history.

(56) References Cited

U.S. PATENT DOCUMENTS

2008/0319508 A1* 12/2008 Botros ............... A61N 1/36039
                                                    607/57
2017/0080229 A1    3/2017 Meister et al.

FOREIGN PATENT DOCUMENTS

WO    WO 2005/122887 A2    12/2005
WO    WO 2005/122887 A3    12/2005
WO    WO 2017/218386 A1    12/2017

OTHER PUBLICATIONS

Botros et al., "AutoNRT™ An automated system that measures ECAP thresholds with the Nucleus® Freedom™ cochlear implant via machine intelligence", Artificial Intelligence in Medicine, Apr. 29, 2007, vol. 40, No. 1, p. 15-28.

(Continued)

*Primary Examiner* — George R Evanisko
(74) *Attorney, Agent, or Firm* — Birch, Stewart, Kolasch & Birch, LLP

(57) ABSTRACT

A method of calibrating stimulation threshold levels of a cochlear implant, comprises sending a series of stimulation signals having a predetermined length in time to a selected subset of a plurality of stimulation electrodes of the cochlear implant of a user, wherein for each signal of the series of stimulation signals, the stimulation level is larger compared to the stimulation level of the previous stimulation signal; receiving an electrophysiological signal for each stimulation signal from a measurement electrode attached to the head of the user; calculating a cross-correlation signal for each of the received electrophysiological signals for each stimulation level following the first stimulation signal with respect to the first electrophysiological signal received for the first stimulation signal, determining, whether the respective cross-correlation signal exceeds a predetermined threshold level, wherein the sending of the series of stimulation signals is stopped and the stimulation level is set as the threshold stimulation level for the selected subset of stimulation electrodes, in case it is determined that the cross-correlation signal exceeds the predetermined threshold level for a first time, and outputting the level of stimulation at which the sending is stopped.

14 Claims, 8 Drawing Sheets

(56) References Cited

OTHER PUBLICATIONS

Charras et al., "Comparison of Two Different Methods to Automatically Classify Auditory Nerve Responses Recorded with NRT System", ACTAAcustica United with Acusitca, May 1, 2004, vol. 90, No. 3, p. 512-519.

* cited by examiner

CROSS-CORRELATION THRESHOLD ESTIMATION METHOD (XTEM)

FIELD

The present disclosure relates to a cross-correlation threshold estimation method (XTEM). More particularly, the disclosure relates to a XTEM for the detection of variations between two signals in the context of electrophysiological measurements for cochlear implant (CI) objective fittings.

BACKGROUND

Before being ready for clinical use, all cochlear implants electrical levels are calibrated for the user of the cochlear implant, i.e. it is required to find each level that induces first audible and most comfortable sound for all activated electrodes. However, the process of fitting the CI typically is very time consuming. Further, the CI fitting process is problematic when a user is not able to inform the audiologist on the sound they can hear, e.g. as in the case of small children or handicapped persons.

Therefore, it is important to find an automatic and objective method to fit CI electrode stimulation levels. For such an automatic and objective method, the inventors have found that subjective (fittings) and objective (eCAPs) thresholds are correlated.

Typical waveforms, delays and amplitudes of electrophysiological responses to external stimulations are well-known. However, near-threshold responses are frequently mixed with noise and therefore difficult to distinguish from noise signals.

Hence, conventional automatic detection telemetries (e.g. autoNRT©) are based on a threshold estimation method using a regression using signals from several supra-threshold stimulations. This leads to time-consuming measurements with potential overstimulation of the cochlea of the user, which is very uncomfortable for the user of the cochlear implant.

Therefore, there is a need to provide a solution that addresses at least some of the above-mentioned problems.

SUMMARY

According to an aspect, a method of calibrating stimulation threshold levels of a cochlear implant comprises the steps of sending a series of stimulation signals, receiving an electrophysiological signal for each stimulation signal, calculating a cross-correlation signal, determining, whether the respective cross-correlation signal exceeds a predetermined threshold level, and outputting the level of stimulation at which the sending is stopped. The step of sending a series of stimulation signals comprises sending a series of stimulation signals having a predetermined length in time to a selected subset of a plurality of stimulation electrodes of the cochlear implant of a user, wherein for each signal of the series of stimulation signals, the stimulation level is larger compared to the stimulation level of the previous stimulation signal. The step of receiving an electrophysiological signal for each stimulation signal comprises receiving an electrophysiological signal for each stimulation signal from a measurement electrode attached to the head of the user. The step of calculating a cross-correlation signal comprises calculating a cross-correlation signal for each of the received electrophysiological signals for each stimulation level following the first stimulation signal with respect to the first electrophysiological signal received for the first stimulation signal. The steps of determining comprises determining, whether the respective cross-correlation signal exceeds a predetermined threshold level, wherein the sending of the series of stimulation signals is stopped and the stimulation level is set as the threshold stimulation level for the selected subset of stimulation electrodes, in case it is determined that the cross-correlation signal exceeds the predetermined threshold level for a first time.

This allows for providing a method for measuring the hearing threshold levels for a user, wherein the user does not feel uncomfortably due to an overstimulation of the cochlea by the stimulation electrodes. Furthermore, an active user interaction is not required for determining the hearing thresholds, so that the process can be used to determine hearing threshold levels of persons, which are unable to communicate for various reasons.

In the method, the stimulation signal may be increased by a predetermined first stimulation level stepwidth.

In the method, if the cross-correlation signal exceeds the predetermined threshold level for the first time, the sending of the series of stimulation signals may be resumed, wherein for each stimulation signal of the resumed series of stimulation signals, the stimulation level is smaller compared to the stimulation level of the preceding stimulation signal by a second stimulation level stepwidth, which is smaller than the first stimulation level stepwidth, and it may be determined, whether the respective cross-correlation signal calculated for each of the received electrophysiological signals for each stimulation level of the resumed series of stimulation signals falls below the predetermined threshold.

This allows for providing an experience of an improved listening situation to the user because the cross-correlation signal becomes lower than the predetermined threshold level.

In the above method, the sending of series of stimulation signals may be further resumed, wherein for each stimulation signal of the further resumed series of stimulation signals, the stimulation level is larger compared to the stimulation level of the preceding stimulation signal by a third stimulation level stepwidth, which is smaller than the second stimulation level stepwidth, and it may be determined, whether the respective cross-correlation signal calculated for each of the received electrophysiological signals for each stimulation level of the further resumed series of stimulation signals exceeds the predetermined threshold for a second time.

This allows for providing an experience of an improved listening situation to the user because the cross-correlation signal is even closer to the predetermined threshold level.

In the above method, the sending of the series of stimulation signals may be again stopped and the level of stimulation may be set as the threshold stimulation level for the selected subset of stimulation electrodes, and the stimulation level at which the sending is stopped for the second time may be output.

In the method, the determination whether the cross-correlation signal exceeds a predetermined threshold level may be based on a difference between the largest value of the cross-correlation signal calculated at a time of stimulating the selected subset of stimulation electrodes and the largest value of the cross-correlation signal calculated at a time where no stimulation of the stimulation electrodes is present.

In the method, the predetermined threshold level may be determined in advance corresponding to the value of one standard deviation of the distribution function of the values of the cross-correlation signals at a time where no stimulation of the stimulation electrodes is present.

In the method, the calculation of the cross-correlation may be based on a normalized sum of a convolution of one electrophysiological signal with a second electrophysiological signal shifted in time.

In a second aspect, a hearing device calibration system is provided, comprising a cochlear implant implanted to a cochlear of an user; a measurement electrode attached to the head of the user; and a processing device, configured to implement the method according to any of the disclosed aspects.

This allows integrating the signal processing method into a hearing aid.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
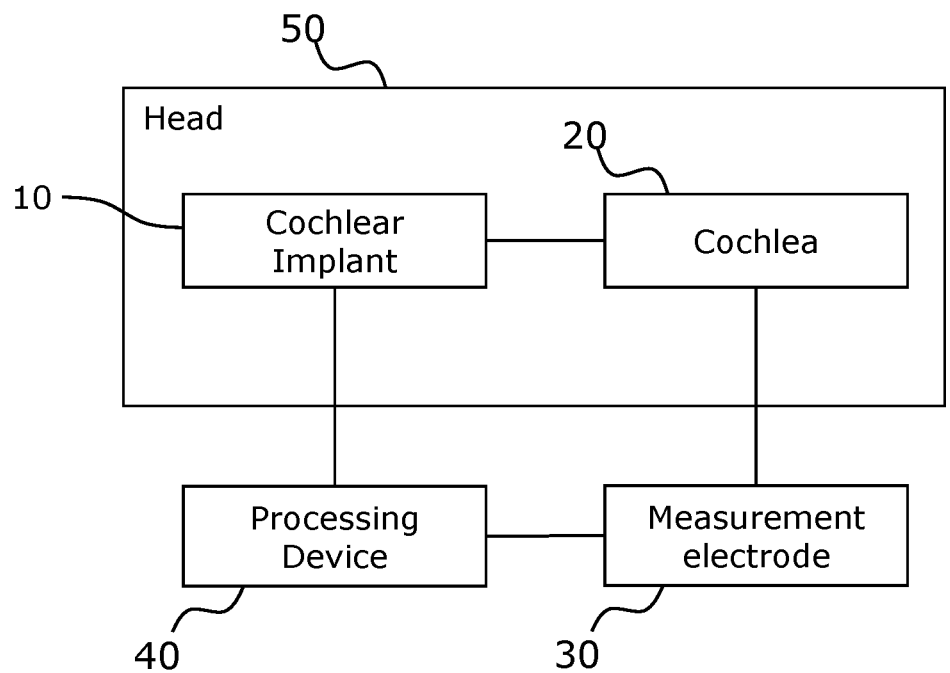
FIG. 1 illustrates a schematic setup for a cochlear implant calibration method according to an embodiment of the disclosure.

Start with Some Boilerplate "Non-Limiting" Language:

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

In the following, an overview over a cross-correlation estimation method is given. The cross-correlation estimation method (XTEM) is a signal detection algorithm. The XTEM is configured to compare two measurement signal traces, and to determine whether there is a difference between two portions of the measurement signals in a given time window.

In view of automatic measurements for a CI fitting method, it is known that an electrophysiological response increases with stimulation intensity. The XTEM is a method to track a variation of an electrophysiological response in a given time window. This variation needs to be higher than a noise floor between the two measurements. If such variation being higher than the noise floor is detected, the criterion is positive. It is noted that the XTEM is not limited to eCAP recordings, but can be implemented to track the presence/absence of any electrophysiological response signal or any electrophysiological recordings. The XTEM is described in more detail below.

Automatic telemetry using a combination of the XTEM with a dichotomic procedure will allow faster and safer threshold estimations, while it will further will bring the detected threshold levels closer to the real hearing impression of the user.

This section describes the calculation methods in order to calculate the cross-correlation criterion (XTE criterion), which is used to decide whether to proceed with increasing/decreasing of the stimulation levels during eCAP measurements.

The XTE criterion value is calculated from a maximum of a plurality of vectors calculated from a cross-correlation between two measurement traces in two different time windows. Note that in the present application, "X" generally denotes the physical portion (the data) of a recording, "R" denotes a calculated cross-correlation between two recordings, while "S" denotes a signal time window (a time window, where a detectable signal is expected), and "N" denotes a noise time window (a time window, where no signal is expected). Hence, "XS" denotes the physical portion of a recording in a time window where a signal is expected to be comprise in the signal, and "XN" denotes the physical portion of a recording in a time window, where no signal is expected, but only noise. "RS" and "RN" denote the respective cross-correlations in a signal time window and in a noise time window.

Further "RS1" denotes a cross-correlation between the 1st and 2nd signals calculated for the XS time window, "RS2" denotes the cross-correlation between the 1st and the 3rd signals in the same window, and so on. Furthermore, "RN1" denotes the cross-correlation between the 1st and 2nd signals calculated for the XN time window, "RN2" denotes the cross-correlation between the 1st and 3rd signals calculated in the same window.

Figure 5:
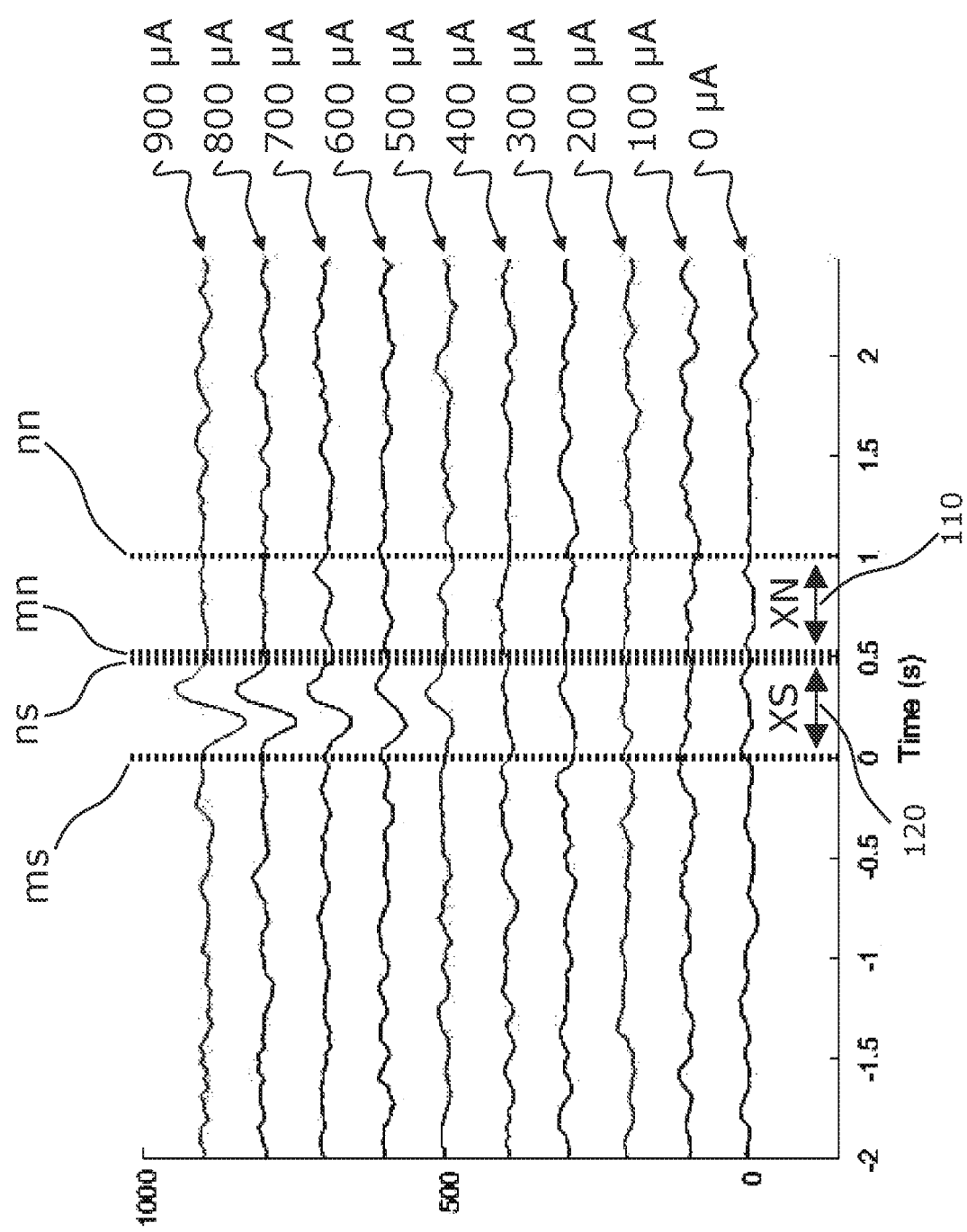
FIG. 5 illustrates time traces for different levels of stimulation as an example.

Equation 1 shows how to calculate a first cross-correlation value RS from two measurements denoted x and y at a given time window between ms and ns (see FIG. 5). As mentioned before, this window is a time window, where a signal is expected to occur (cf. the time window indicated by the two vertical dotted lines in the FIG. 5, ref. sign 120), that is, after a stimulation pulse, typically a response appears in the respectice eCAP measurements in a certain time window.

As shown in FIG. 5, by using a large stimulation value, an eCAP signal can be detected. The signal time window is then set accordingly to comprise this eCAP response to the stimulation value. The noise time window is set to be after the signal time window, having the same length. Note that in the example of FIG. 5, the windows have the same length, but the invention is not limited to the windows having the same length, but the lengths can be different as well.

The cross-correlation value RS in the signal time window, is defined in Equation 1.

$$RSyx(ms) = \frac{1}{T-ms+1} \sum_{ns=1}^{T-ms+1} (y(ns)x(ns+ms-1)) \quad \text{(Eq. 1)}$$

Here, ms=1, 2, 3, ..., T, wherein T is the number of samples in the time window.

Equation 2 shows the second cross-correlation RN between two eCAP measurements noted x and y, in a noise time window between mn and nn, where there is no eCAP response is expected. Further, in FIG. 5 accordingly, no response signal can be seen (cf. the time window indicated by the vertical dotted lines in the FIG. 5, ref. sign 110). RS and RN may have different number of samples, as mentioned before.

$$RNyx(mn) = a_0 \sum_{nn=1}^{N-mn+1} (y(nn)x(nn+mn-1)) \quad \text{(Eq. 2)}$$

Here, $a_0$ is a normalization factor $a_0=1/(N-mn+1)$, while ε represents a noise floor error estimation based on prediction intervals (to be calculated below). It is not necessary to calculate Equation 1 before Equation 2, and Equation 2 may be calculated before calculating Equation 1.

However, afterwards, XS and XN can be calculated as follows:

$$XS=\max[RS_{yx}(m_s)] \quad \text{(Eq. 3)}$$

and $$XN=\max[RN_{yx}(m_s)] \quad \text{(Eq. 4)}$$

Using the normal cumulative distribution function of RN, a noise floor margin ε can be calculated from the Equation 6. ε represents the noise floor error estimation based on prediction intervals.

$$\varepsilon=(\max[RN_{yx}(m_s)])*(\text{norminv}(\text{std}(\max[RN_{yx}(m_s)]))) \quad \text{(Eq. 5)}$$

Here, "norminv" represents the inverse of the cumulated normal distribution, and "std" represents the standard deviation σ. Hence, it can be said that the error margin ε is calculated to be equal to the standard deviation a of the data $RN_{yx}$ representing the signal correlation of the two signal measurements x and y in the noise time window.

The XTE criterion value can be calculated by the subtracting XN from XS by taking into account the noise floor margin ε by the formula given in Equation 6.

$$XTE=XS-(XN+\varepsilon)=\max[RSyx(ms)]-\max[RNyx(ms)]-\varepsilon \quad \text{(Eq. 6)}$$

The XTE criterion is determined to be positive ("YES"), in case the XTE criterion value is larger than 0, and the XTE criterion is determined to be negative ("NO") otherwise.

That is, the XTE criterion determines, whether the cross-correlation signal exceeds a margin of one standard deviation above a maximum value of the signal correlation in the noise time window.

In the following paragraph, an example for the cross-correlation threshold estimation method is given in the case of processing for eCAP signals. eCAP signals are electrophysiological signals recorded directly by cochlear implants. FIG. 5 shows example signal traces (curves) for an eCAP signal in response of 10 different stimulus intensities as a function of time. The stimulus intensities are denoted on the right side of the Fig. (from bottom (0 μA) to top (900 μA)). The abzissa axis in FIG. 5 denotes a time difference to an impulse given by the respective electrode. The ordinate axis respresents a scale of a response signal level (arbitrary units), while the response curves are offset for clarity. The eCAP signals are centred to 0 seconds. eCAP signal responses are shown to increase as the stimulus intensity increases from 0 μA to 900 μA.

The vertical dotted lines denoted "ms" and "ns" represent a time window 120, where the eCAP response is supposed to occur, and the vertical dotted lines denoted "mn" and "nn" represent a time window 110 recording only noise. The first response is visible for levels between 500 and 600 μA in the time window 120.

Figure 6A:
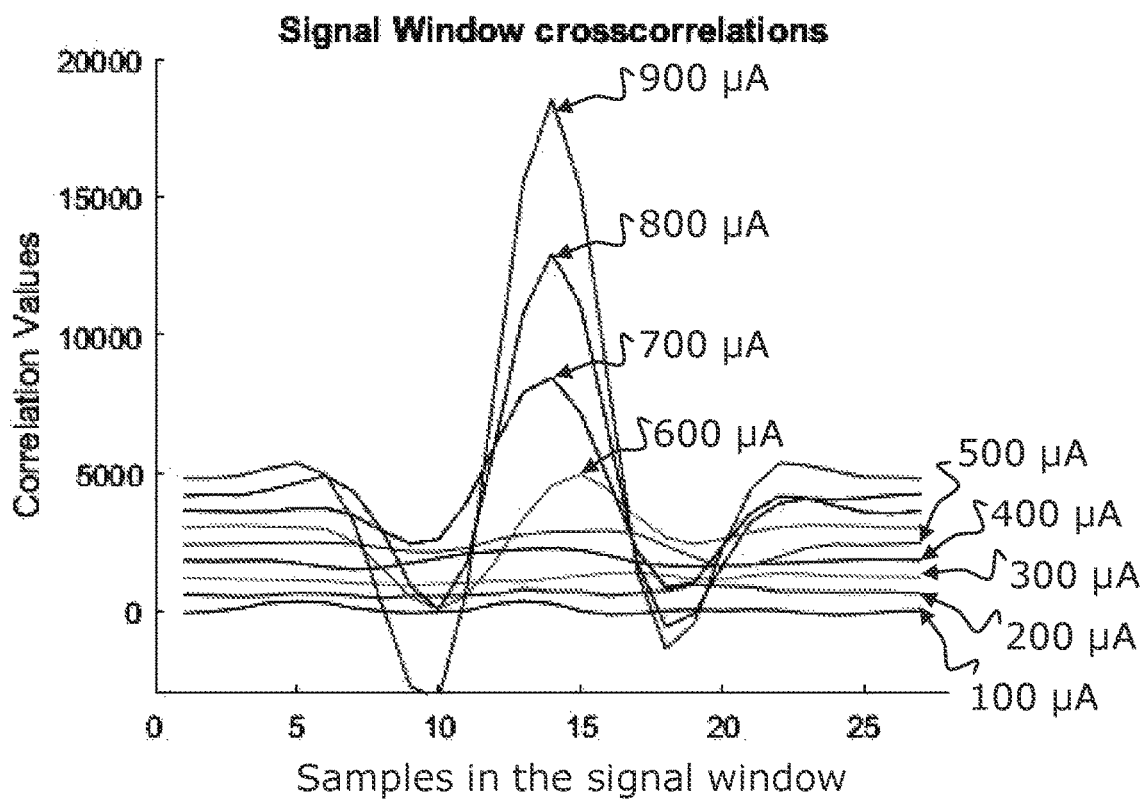
FIG. 6A is a graph illustrating cross-correlation signals for different levels of stimulation in case a stimulation is present.

FIG. 6A shows the RS cross-correlations (cf. Eq. 1), i.e. all cross-correlations of two measurements (0 μA correlated with 100 μA, 0 μA correlated with 200 μA, . . . , 0 μA correlated with 900 μA) cross-correlations in the signal time window, cf. FIG. 5, time window 120. That is, FIG. 6A shows a representation of an autocorrelation vector for each curve of FIG. 5 other than "0 μA", wherein each curve of FIG. 5 is correlated with curve "0 μA" of FIG. 5. The abszissa axis in FIG. 6A denotes the number of samples in the signal window, that is, the time window 120 in FIG. 5, while the ordinate axis respresents the calculated correlation values.

Figure 6B:
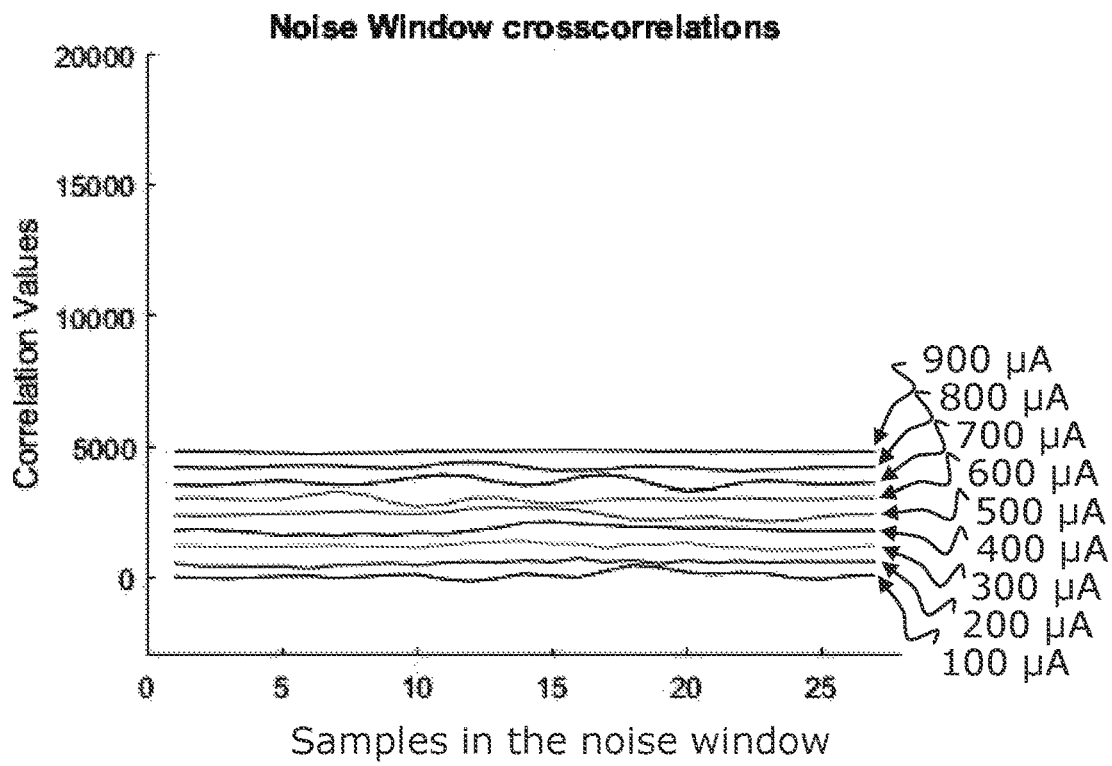
FIG. 6B is a graph illustrating cross-correlation signals for different levels of stimulation at a time where no signal is present.

FIG. 6B represents the RN autocorrelation (cf. Eq. 2), i.e. the cross-correlation in the noise time window 110, cf. FIG. 5, in the same way as FIG. 6A, however calculated for time window 110.

Figure 7:
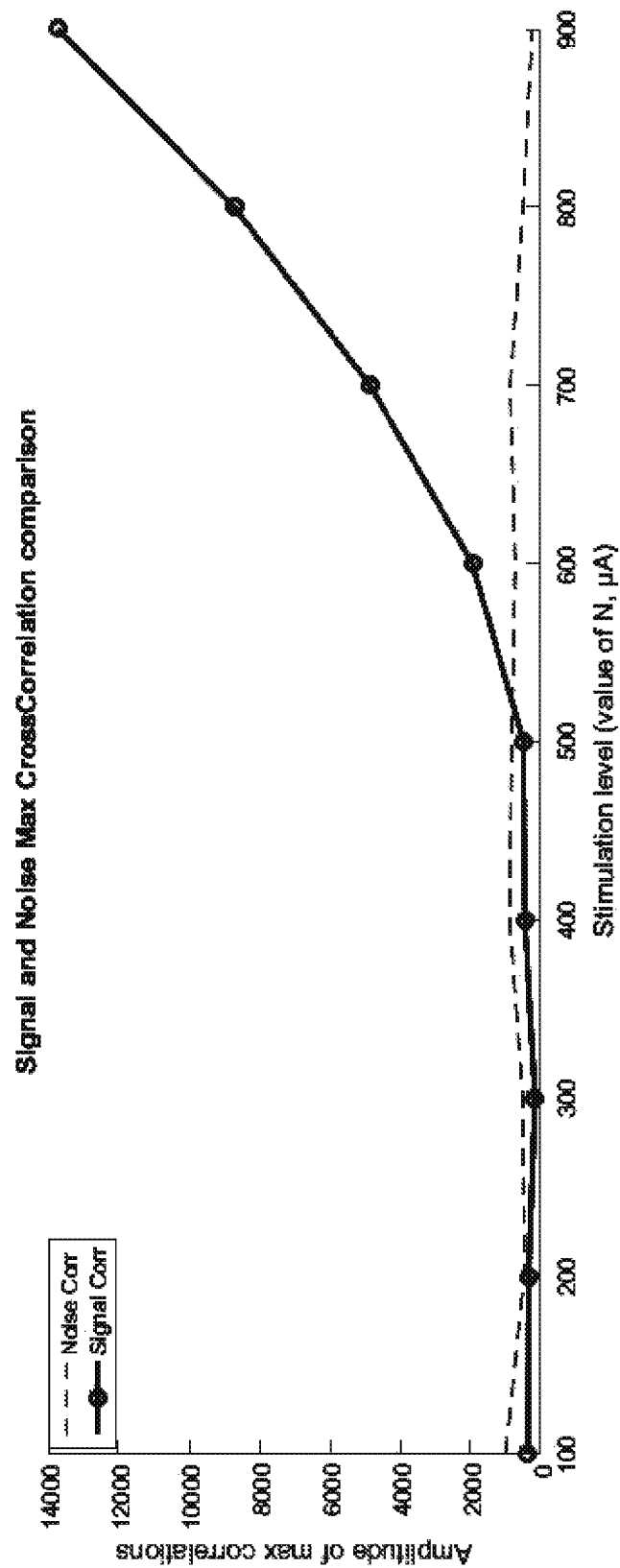
FIG. 7 is a graph illustrating comparison between different cross-correlation signals.

FIG. 7 represents the XS ("Signal Corr", straight line) and XN ("Noise Corr", dashed line) functions dependent on the stimulation level. FIG. 7 shows all XS and XN+ε values calculated from Eq. 1 and 2. When the XTE criterion is negative, i.e. in case XS≤XN+ε, the signal is considered to be free (empty) of an eCAP signal response (<noise floor ε). When the XTE criterion is positive, i.e. XS >XN+ε, this means, that a response is detected (i.e. a variation higher than the noise floor ε is present). In FIG. 7, at a stimulation level of 600 μA and higher, the signal correlation value is larger than the noise floor.

In the following, an example of an application using the XTE criterion is described with reference to FIG. 8, which is a graph for illustrating a method according to an embodiment of the disclosure. The method is the XTEM, which makes use of the XTE criterion. This method is a dichotomic method, in other words, a method, which determines one of two possibilities in each cycle.

Figure 8:
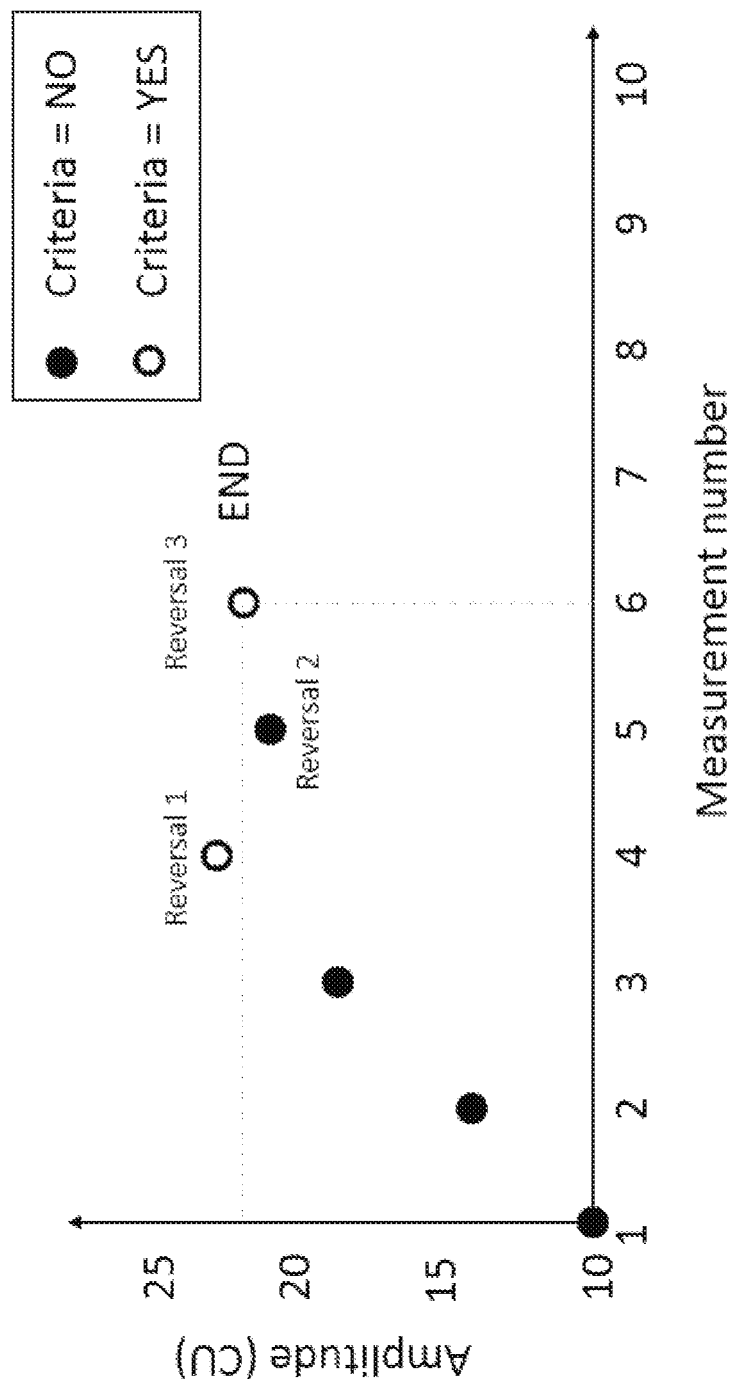
FIG. 8 is a graph for illustrating a method according to an embodiment of the disclosure.

Regarding FIG. 8, an example procedure is shown, in which the XTEM is used. In the method according to the invention, the XTE criterion is used to determine the next step of the procedure. This criterion controls, whether the current stimulation level is increased or decreased, the amount of increase or decrease, or whether the procedure is stopped.

In FIG. 8, the horizontal axis shows the measurement number, that is the iteration number of the method. The vertical axis shows the amplitude of stimulation that is given to a certain simulation electrode in units of current level units. The dichotomic progression of deciding of the electrical levels to generate in function of the Cross-correlation criterion C. This progression makes current levels reversals, each reversal resulting in dividing current stepsize by a factor of 2.

At first, a signal (reference signal) is recorded without stimulating the electrode (before the start of the method). According to FIG. 8, in the first iteration an stimulation signal level of 10 current level units (CU) is applied to the electrode. During the stimulation a first signal trace is recorded by performing an eCAP measurement using the electrode. Subsequently, the XTE criterion value is calculated using the first signal and the reference signal. In FIG. 8, it is for the first iteration indicated that the criteria on is negative, that is, the criteria=NO. The method therefore advances to the second iteration by increasing the stimulation value by a stepsize of +4 CU.

In the second iteration a stimulation signal level of 14 current level units is applied to the electrode, while a second signal trace is recorded by performing an eCAP measurement using the electrode. Subsequently, the XTE criterion value and the XTE criterion are calculated using the second signal and reference signal. In FIG. 8, it is indicated that again the XTE criterion=NO. The method therefore advances to the third iteration by again increasing the stimulation value by a stepsize of +4 CU.

The method is further iterated, until the calculated XTE criterion results in YES. In the present case, in FIG. 8, this happens at iteration 4. At this point (Reversal 1), the stimulation value will be subsequently decreased by 2 CU (the stepsize being −2 CU), and the method is continued.

Alternatively, it can be said that the stepsize is divided by 2 (a reduction in current level with a stepsize two times lower) and the sign of the stepsize is reversed. Until the XTE criterion changes again to NO, the stimulation signal level will subsequently be decreased.

That is, the stimulation level will keep decreasing as long as response is detected. When no more response is detected using the XTE criterion, the method creates a second reversal in current level, and stepsize is set to be two times lower.

That is, if the XTE criterion changes for the second time, the stimulation signal level is subsequently increased again. However, the stepsize is again divided by 2, and the sign of the stepsize is reversed. In the present case, according to FIG. 8, this happens at iteration 5, and the stepsize is set therefore to +1 CU.

At iteration 6, the XTE criterion changes again to YES, which ends the method. The stimulation signal level in this last step is now taken as the hearing threshold stimulation level for this specific electrode. That is, the XTEM ends when the third reversal is detected. Hence, the current stepsize starts with +4 CU, is decreased to −2 CU, and finally decreased to +1 CU.

Hence, FIG. 8 shows an example of progression of a dichotomic procedure in the context of eCAP threshold tracking. The initial stepsize level is fixed at 4 CU, however can be set to any other suitable value. The procedure in the example of FIG. 8 needs 6 measurements, if the threshold is close to 21 CU.

One advantage of this method is, that an overstimulation of the cochlea of the user is very unlikely to happen, that is the method is more comfortable for the user. Furthermore, this method can be automated in such a way that the above-described XTEM is performed for each electrode, one by one. Therefore, the method is also faster than conventional methods which require user interaction.

In the description above, the current level is described in units of "1 CU", that is "one current level unit". 1 CU can for example be 100 µA, but can be set to any other suitable current level.

Now referring to FIG. 1, which illustrates a schematic setup for a cochlear implant calibration method according to an embodiment of the disclosure. A cochlear implant 10 is provided in a cochlea 20, which is located in a head 50 of the user.

The cochlea 20 may be the cochlea of a right ear or a left ear of the user. Signals detected by the cochlear above the hearing threshold are suitable to be heard by the user, that is, the signals are transferred to the brain of the user, and therefore can be detected by a measurement electrode 30, or by a respective electrode of the cochlear implant 10.

The measurement electrode 30 is an electrode of the electrode array of the cochlear implant. Signals registered by the measurement electrode 30 will be transferred to the processing device 40.

The processing device 40 records signals from the measurement electrode 30, and can communicate with external devices (not shown) to transfer the signals for further processing by an external device.

The processing device 40 can also receive control information or control signals to generate stimulation signals, which are sent to the cochlear implant 10. Stimulation signals sent to the cochlear implant 10 are transmitted to the stimulation electrodes of the electrode array, which is implanted into the cochlea 20.

The processing device 40 is configured to perform the XTEM, that is, the cross-correlation threshold estimation method.

Figure 2:
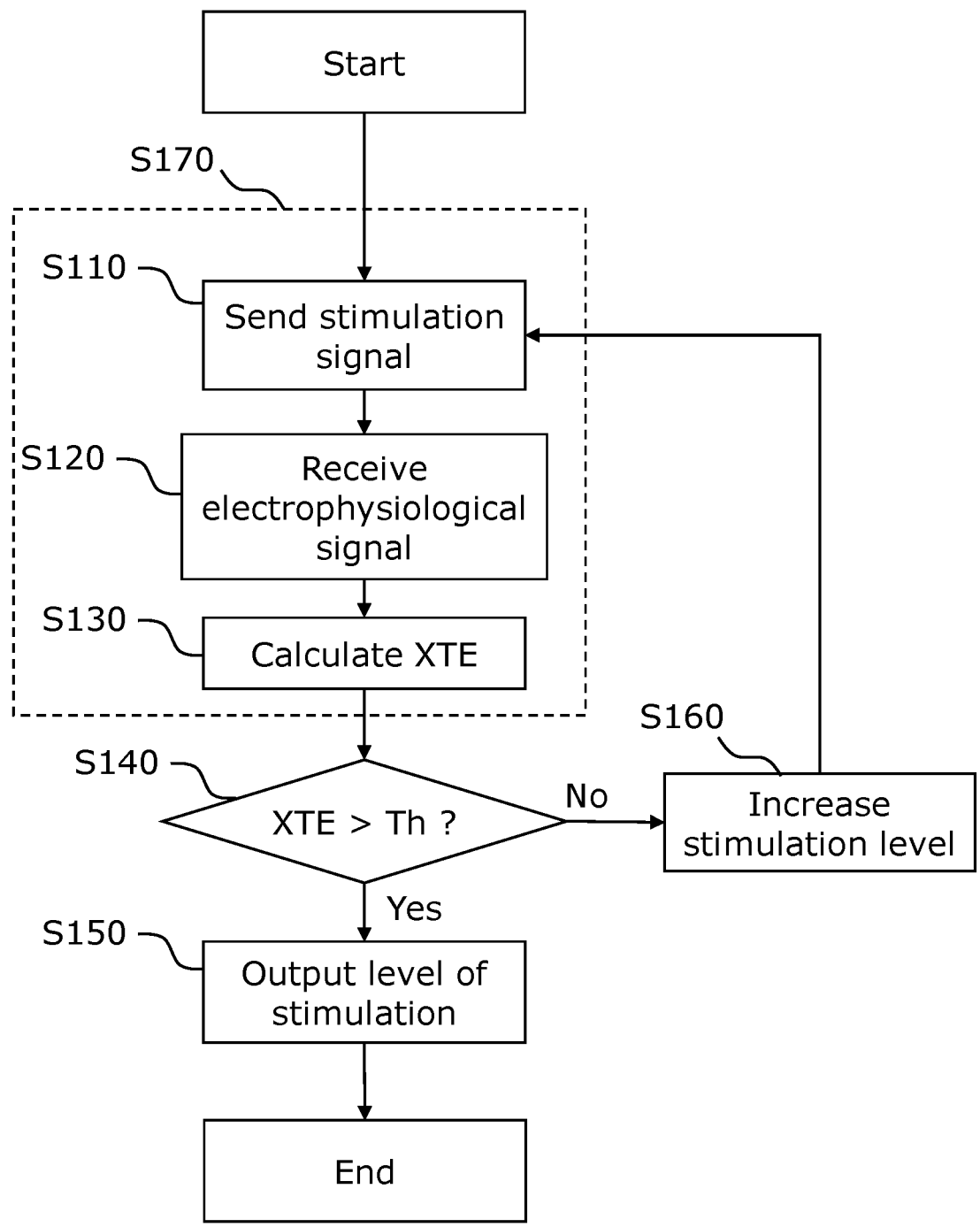
FIG. 2 illustrates a flow diagram describing a method according to an embodiment of the disclosure.

Now referring to FIG. 2, FIG. 2 illustrates a flow diagram describing a method according to an embodiment of the disclosure. Before the start of the method, and an electrode is selected as the selected electrode, for which the method is performed.

At the start of the method, the stepsize is set to a predetermined stepsize level (e.g., 4 CU), and the stimulation current level is set to a predetermined start current level. A reference signal is recorded by the measurement electrode of the selected electrode with no stimulation present. The procedure advances subsequently to step S110.

In S110, a stimulation signal having the stimulation current level is sent to the selected electrode of the cochlear implant 10. Subsequently, the method proceeds to step 120.

In S120, a signal trace is recorded by performing an eCAP measurement using the selected electrode. It is noted, that the steps S110 and S120 are performed in parallel, so that the signal trace can be recorded while the stimulation signal is sent. Subsequently, the method proceeds to step S130.

In step S130, the XTE criterion value is calculated according to the equations Eq. 1 to Eq. 6. Subsequently, the method proceeds to step S140.

The steps S110, S120, S130 can be grouped together as one step S170. s170 is called "measuring the XTE criterion".

In step S140, the method decides whether the XTE criterion value is larger than the threshold Th. Typically, Th is 0. However, Th can be any other value, suitable for a precise determination of the presence of a signal response. If the XTE criterion value is larger than Th, the procedure advances to S150. If the XTE criterion value is not larger than Th, the procedure advances to step S160.

In step S160, the stimulation level is increased by adding the value of the stepsize. Afterwards, the procedure advances to step S110.

In step S150, it is determined, that the method is ended. The stimulation signal level as used in S110 in the present iteration is taken as the electrode stimulation level for the selected electrode and for example, output to an external device. The procedure is afterwards ended.

The method as shown in FIG. 2 has the advantage of following a simple protocol, having the advantage of being very fast. However, it is possible to the determine the hearing threshold level more precisely. This can be done by the method shown in FIG. 3, which is described in the following.

Figure 3:
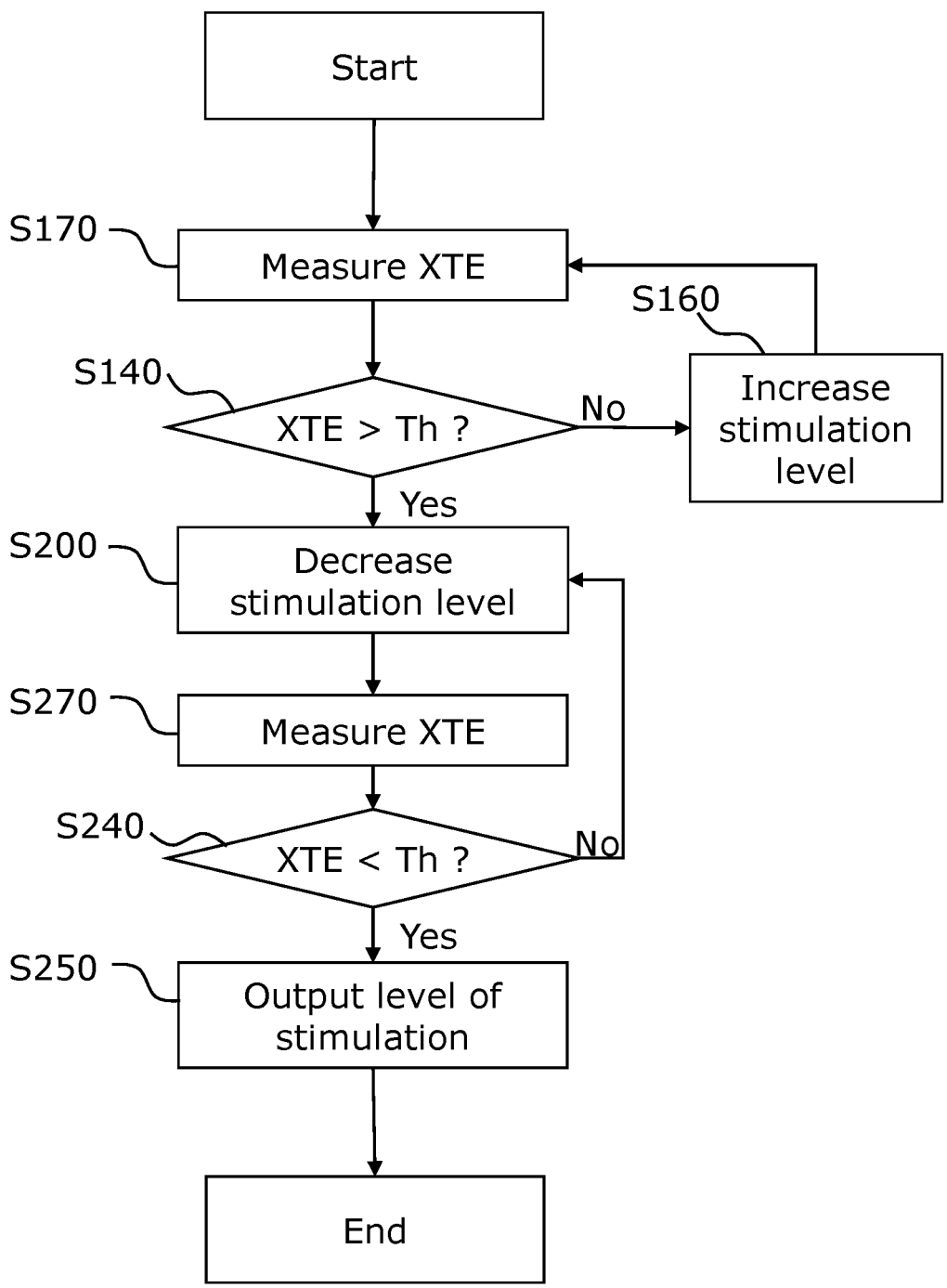
FIG. 3 illustrates a flow diagram describing a method according to an embodiment of the disclosure.

FIG. 3 illustrates a flow diagram describing a method according to an embodiment of the disclosure. As with the procedure shown in FIG. 2, at the start of the method, the stepsize is set to a predetermined stepsize level (e.g, 4 CU), and the stimulation current level is set to a predetermined start current level. A reference signal is recorded by the measurement electrode of the selected electrode with no stimulation present. The procedure advances subsequently to step S170.

In S170, the XTE criterion is measured. That is, a stimulation signal having the stimulation current level is sent to the selected electrode of the cochlear implant 10. Further, a signal trace is recorded by performing an eCAP measurement using the selected electrode. It is noted, that the sending of the stimulation signal is performed in parallel with the recording of the eCAP measurement, just as described before in steps S110 and S120. Furthermore, the XTE criterion value is calculated according to the equations Eq. 1 to Eq. 6, as in step S130 according to FIG. 2. Subsequently, the method proceeds to step S140.

In step S140, the method decides, whether the XTE criterion value is larger than the threshold Th, as explained above in conjunction with step S140 of FIG. 2. If the XTE criterion value is larger than Th, the procedure advances to S200. In this case, the stepsize is lowered by half, that is, the stepsize value is divided by 2. If the XTE criterion value is not larger than Th, the procedure advances to step S160.

Step S160 is the same as step S160 in FIG. 2. Subsequently, the method returns to step S170.

In step S200, the stimulation level is decreased the stepsize value. Subsequently, the method advances to step S270. Step S270 is similar to step S170, that is, the XTE criterion is measured. In other words, a stimulation signal is sent to the selected electrode, a signal trace is recorded, and the XTE criterion value is calculated as explained before. Subsequently, the method advances to step S240.

In step S240, the method decides, whether the XTE criterion value is smaller than the threshold Th, similar to step S140 FIG. 2, however having an inverted inequality equation. If the XTE criterion value is lower than Th, the procedure advances to S250. In this case, the stepsize is lowered by half, that is, the stepsize value is divided by 2. If the XTE criterion value is not lower than Th, the procedure advances to step S200.

In step S250, it is determined, that the method is ended. The stimulation signal level as used in the last stimulation step (S270) is taken as the electrode stimulation level for the selected electrode, and is, for example, output to an external device. The procedure is afterwards ended.

The method as shown in FIG. 3 allows for providing an experience of an improved listening situation to the user, because the cross-correlation signal becomes lower than the hearing threshold level of the user.

However, it is possible to the determine the hearing threshold level even more precisely. This can be done by the method shown in FIG. 4, which is described in the following.

Figure 4:
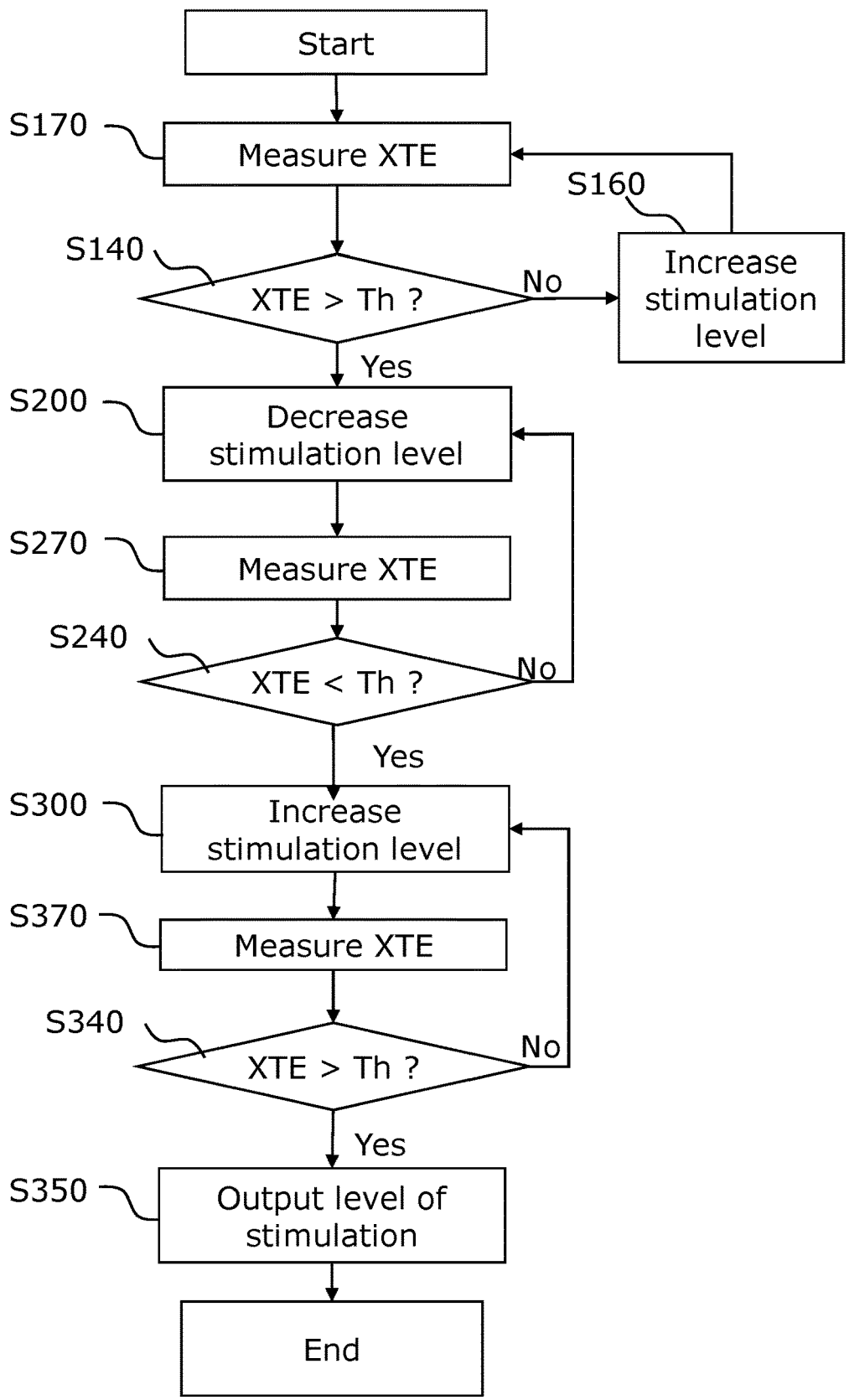
FIG. 4 illustrates a flow diagram describing a method according to an embodiment of the disclosure.

FIG. 4 illustrates a flow diagram describing a method according to an embodiment of the disclosure.

As with the procedures of FIG. 2 and FIG. 3, the method is starting by setting the initial values as before. Steps S170, S140, S160, S200, S270 are the same as in the procedure shown in FIG. 3.

Once, the procedure advances to step S240, it is again decided, similar to the step S240 in FIG. 2, whether the XTE criterion value is lower than Th. If the XTE criterion value is lower than Th, the procedure advances to step S300, and lowers the stepsize by half, that is, the stepsize is divided by 2. If the XTE criterion value is not lower than Th, the procedure advances to step S200.

In step S200, the stimulation signal level is increased by the stepsize. Subsequently, the procedure advances to step S370.

In step S370, as in steps S270 and S170, the XTE criterion is measured. Subsequently the procedure advances to step S340.

In step S340, the same decision is taken as in step S40, that is, it is determined whether the XTE criterion value is larger than Th. If the XTE criterion value is larger than Th, the procedure advances to step S350, otherwise, the procedure returns to S300.

In step S350, it is determined, that the method is ended. The stimulation signal level as used in the last stimulation step (S370) is taken as the electrode stimulation level for the selected electrode, and is, for example, output to an external device. The procedure is ended afterwards.

The method according to FIG. 4 allows to determine the hearing threshold level even more precisely as the procedures shown in FIG. 2 and FIG. 3.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

A Computer Readable Medium

In an aspect, the functions may be stored on or encoded as one or more instructions or code on a tangible computer-readable medium. The computer readable medium includes computer storage media adapted to store a computer program comprising program codes, which when run on a processing system causes the data processing system to perform at least some (such as a majority or all) of the steps of the method described above, in the and in the claims.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium. For example, the procedures shown in FIG. 2, FIG. 3, and FIG. 4 can be realized in software.

A Data Processing System

In an aspect, a data processing system comprising a processor adapted to execute the computer program for causing the processor to perform at least some (such as a majority or all) of the steps of the method described above and in the claims. For example, the procedures shown in FIG. 2, FIG. 3, and FIG. 4 can be realized in software.

It is intended that the structural features of the devices described above, either in the detailed description and/or in the claims, may be combined with steps of the method, when appropriately substituted by a corresponding process.

End the Detailed description with some boilerplate. *The Federal Circuit recently relied on this exact language in Honeywell Int'l, Inc. v. United States, to expand patent rights.* 596 *F.*3d 800, 807-10 (*Fed. Cir.* 2010). As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A method of calibrating stimulation threshold levels of a cochlear implant, comprising:
   sending a series of stimulation signals having a predetermined length in time to a selected subset of a plurality of stimulation electrodes of the cochlear implant of a user, wherein for each signal of the series of stimulation signals, the stimulation level is larger compared to the stimulation level of the previous stimulation signal;
   receiving an electrophysiological signal for each of the sent stimulation signals from a measurement electrode attached to the head of the user;
   calculating a cross-correlation signal for each of the received electrophysiological signals for each of the stimulation levels of the stimulation signals sent following the first sent stimulation signal with respect to the first electrophysiological signal received for the first stimulation signal,
   calculating a largest value of the respective cross-correlation signal at a time of stimulating the selected subset of stimulation electrodes,
   calculating a largest value of the respective cross-correlation signal at a time where no stimulation of the stimulation electrodes is present,
   obtaining a difference between the largest value of the respective cross-correlation signal calculated at the time of stimulating the selected subset of stimulation electrodes and the largest value of the respective cross-correlation signal calculated at the time where no stimulation of the stimulation electrodes is present,
   determining, based on the obtained difference, whether the respective cross-correlation signal exceeds a predetermined threshold level,
   stopping the sending of the series of stimulation signals, and setting the current stimulation level as the threshold stimulation level for the selected subset of stimulation electrodes, when the determination is made that the calculated cross-correlation signal exceeds the predetermined threshold level for a first time, and
   outputting the current level of stimulation at which the sending is stopped.

2. The calibration method according to claim 1, wherein the sending of the series of stimulation signals includes,
   increasing the stimulation signal by a predetermined first stimulation level stepwidth.

3. The calibration method according to claim 2, further comprising, after the cross-correlation signal exceeds the predetermined threshold level for the first time,
   resuming the sending of the series of stimulation signals in such manner that, for each stimulation signal of the resumed series of stimulation signals, the stimulation level is smaller compared to the stimulation level of the preceding stimulation signal by a second stimulation level stepwidth, which is smaller than the first stimulation level stepwidth, and
   determining whether the respective cross-correlation signal calculated for each of the received electrophysiological signals for each of the stimulation levels of the resumed series of stimulation signals falls below the predetermined threshold.

4. The calibration method according to claim 3, further comprising, after determining that the cross-correlation signal falls below the predetermined threshold,
   further resuming the sending of series of stimulation signals in such manner that, for each stimulation signal of the further resumed series of stimulation signals, the stimulation level is larger compared to the stimulation level of the preceding stimulation signal by a third stimulation level stepwidth, which is smaller than the second stimulation level stepwidth, and
   further determining whether the respective cross-correlation signal calculated for each of the received electrophysiological signals for each of the stimulation levels of the further resumed series of stimulation signals exceeds the predetermined threshold for a second time.

5. The calibration method according to claim 4, further comprising,
   stopping the further resumed sending of the series of stimulation signals and setting the current level of stimulation is set as the threshold stimulation level for the selected subset of stimulation electrodes, when the further determination is made that the cross-correlation signal exceeds the predetermined threshold level for the second time, and
   outputting the current stimulation level at which the further resumed sending is stopped.

6. The calibration method according to claim 5, further comprising,
   obtaining a convolution of one electrophysiological signal with a second electrophysiological signal shifted in time, and calculating a normalized sum of the convolution of the one electrophysiological signal with the second electrophysiological signal shifted in time,
wherein the calculation of the cross-correlation is based on the normalized sum of the convolution of the one electrophysiological signal with the second electrophysiological signal shifted in time.

7. The calibration method according to claim 4, further comprising,
obtaining a convolution of one electrophysiological signal with a second electrophysiological signal shifted in time, and
calculating a normalized sum of the convolution of the one electrophysiological signal with the second electrophysiological signal shifted in time,
wherein the calculation of the cross-correlation is based on the normalized sum of the convolution of the one electrophysiological signal with the second electrophysiological signal shifted in time.

8. The calibration method according to claim 3, further comprising,
obtaining a convolution of one electrophysiological signal with a second electrophysiological signal shifted in time, and
calculating a normalized sum of the convolution of the one electrophysiological signal with the second electrophysiological signal shifted in time,
wherein the calculation of the cross-correlation is based on the normalized sum of the convolution of the one electrophysiological signal with the second electrophysiological signal shifted in time.

9. The calibration method according to claim 2, further comprising,
obtaining a convolution of one electrophysiological signal with a second electrophysiological signal shifted in time, and
calculating a normalized sum of the convolution of the one electrophysiological signal with the second electrophysiological signal shifted in time,
wherein the calculation of the cross-correlation is based on the normalized sum of the convolution of the one electrophysiological signal with the second electrophysiological signal shifted in time.

10. The calibration method according to claim 1, further comprising,
determining, in advance, the predetermined threshold level corresponding to the value of one standard deviation of a distribution function of the values of the cross-correlation signals at a time where no stimulation of the stimulation electrodes is present.

11. The calibration method according to claim 10, further comprising,
obtaining a convolution of one electrophysiological signal with a second electrophysiological signal shifted in time, and
calculating a normalized sum of the convolution of the one electrophysiological signal with the second electrophysiological signal shifted in time,
wherein the calculation of the cross-correlation is based on the normalized sum of the convolution of the one electrophysiological signal with the second electrophysiological signal shifted in time.

12. The calibration method according to claim 1, further comprising,
obtaining a convolution of one electrophysiological signal with a second electrophysiological signal shifted in time, and
calculating a normalized sum of the convolution of the one electrophysiological signal with the second electrophysiological signal shifted in time,
wherein the calculation of the cross-correlation is based on the normalized sum of the convolution of the one electrophysiological signal with the second electrophysiological signal shifted in time.

13. A hearing device calibration system, comprising
a processing device configured to implement the method according to claim 1;
the cochlear implant configured to be implanted in the cochlear of the user; and
the measurement electrode configured to be attached to the head of the user.

14. A hearing device calibration system, comprising
a processing device configured to implement the method according to claim 2;
the cochlear implant configured to be implanted in the cochlear of the user; and
the measurement electrode configured to be attached to the head of the user.

* * * * *